United States Patent
Liu et al.

(10) Patent No.: US 6,323,311 B1
(45) Date of Patent: Nov. 27, 2001

(54) SYNTHESIS OF INSULIN DERIVATIVES

(75) Inventors: Feng Liu; Sung Wan Kim; Miroslav Baudys, all of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/400,942

(22) Filed: Sep. 22, 1999

(51) Int. Cl.[7] ............................. A61K 38/28; C07K 14/62
(52) U.S. Cl. ................................. 530/303; 514/3
(58) Field of Search .................... 530/303, 304, 530/305; 514/3.4

(56) References Cited

U.S. PATENT DOCUMENTS

| | | | |
|---|---|---|---|
| 3,868,356 | 2/1975 | Smyth | 530/303 |
| 3,868,357 | 2/1975 | Smyth et al. | 530/303 |
| 3,869,437 | 3/1975 | Lindsay et al. | 530/303 |
| 3,907,763 | 9/1975 | Brandenburg et al. | 530/303 |
| 4,013,628 | 3/1977 | Obermeier et al. | 530/303 |
| 4,179,337 | 12/1979 | Davis et al. | 435/181 |

(List continued on next page.)

FOREIGN PATENT DOCUMENTS

| | | |
|---|---|---|
| 1 156 217 | 11/1983 | (CA) . |
| 24 33 883 | 2/1976 | (DE) . |
| 29 30 542 | 2/1981 | (DE) . |

OTHER PUBLICATIONS

Kimura et al. A Practical Reagent for Reversible Amino . . . Biol. Pharm. Bull. vol. 17, No. 7, pp. 881–885, Jul. 1994.*

Zaitsu et al. Preparation of [3–(2–Pyridyldithio)propionoyl] insulins . . . Chem. Pharm. Bull. vol. 36, No. 4, pp. 1425–1430, 1988.*

Caliceti et al. Successful Insulin Delivery By PEG Conjugation. Proc. Intl. Symp. Control. Rel. Bioact. Mater. vol. 25, pp. 263–264, 1998.*

Veronese et al. Improvement of pharmacokinetic, immunological adt stability . . . J. Controlled Release. vol. 40, pp. 199–209, 1996.*

Miroslav Baudyš, et al.; Physical Stabilization of Insulin by Glycosylation; 28–33; Jan. 1995; Journal of Pharmaceutical Sciences vol. 84, No. 1.

Jan Markussen, et al; Immobilized Insulin for High Capacity Affinity Chromatography of Insulin Receptors; 18814–18818; Oct. 5, 1991; The Journal of Biological Chemistry.

B. Rihova, et al.; Immunogenicity of Glycosylated Derivatives of Insulin. I. Antibodies to Gliadin detected after immnization with Insulin and its G–derivatives; 191–214; 1994; J. Clin. Lab. Immunol.

*Primary Examiner*—Jeffrey E. Russel
(74) *Attorney, Agent, or Firm*—Clayton, Howarth & Cannon, P.C.

(57) ABSTRACT

A method for the "one-pot" synthesis of insulin derivatives wherein insulin is modified at the α-amino group of the PheB1 residue is described. The method comprises protecting the α-amino group of the GlyA1 residue and the ε-amino group of the LysB29 residue by reaction of insulin with a cyclic anhydride of a dicarboxylic acid in the presence of a tertiary amine. The protected insulin is then reacted with an activated hydrophilic compound, preferably an activated polyethylene glycol, resulting in a conjugate of the hydrophilic compound coupled to the PheB1 residue of insulin. The protecting groups are then removed from the conjugate under mild acidic conditions, and the resulting insulin derivative can be purified by conventional methods. Monosubstituted insulin derivatives wherein polyethylene glycol or derivatives thereof or glycosides are coupled to the PheB1 residue of insulin are also described.

20 Claims, 5 Drawing Sheets

U.S. PATENT DOCUMENTS

| | | | |
|---|---|---|---|
| 4,444,683 | 4/1984 | Kim et al. | 530/303 |
| 4,478,746 | 10/1984 | Kim et al. | 530/303 |
| 4,478,830 | 10/1984 | Kim et al. | 514/3 |
| 4,483,792 | 11/1984 | Kim et al. | 530/303 |
| 4,489,063 | 12/1984 | Kim et al. | 514/3 |
| 4,489,064 | 12/1984 | Kim et al. | 514/3 |
| 4,536,572 | 8/1985 | Kim et al. | 536/17.9 |
| 4,601,979 | 7/1986 | Andresen et al. | 435/681 |
| 4,639,332 | 1/1987 | Grau | 530/303 |
| 4,645,740 | 2/1987 | Breddam et al. | 435/71 |
| 4,791,192 | 12/1988 | Nakagawa et al. | 530/399 |
| 4,839,341 | 6/1989 | Massey et al. | 514/4 |
| 4,931,544 * | 6/1990 | Katre et al. | 530/351 |
| 5,015,728 | 5/1991 | Obermeier et al. | 530/303 |
| 5,214,131 | 5/1993 | Sano et al. | 530/345 |
| 5,286,637 | 2/1994 | Veronese et al. | 435/183 |
| 5,359,030 | 10/1994 | Ekwuribe | 530/303 |
| 5,430,110 * | 7/1995 | Ahlers et al. | 525/328.2 |
| 5,506,202 | 4/1996 | Vertesy et al. | 514/3 |

\* cited by examiner

SYNTHESIS OF INSULIN DERIVATIVES

STATEMENT REGARDING FEDERALLY SPONSORED RESEARCH OR DEVELOPMENT

This invention was made with government support under Grant No. DK50557 awarded by the National Institutes of Health. The government has certain rights in the invention.

BACKGROUND OF THE INVENTION

This invention relates to derivatives of insulin that show improved properties as compared to the natural protein. More particularly, the invention relates to an improved method for the synthesis of such insulin derivatives and certain derivatives prepared by this and other methods.

It is well known that insulin consists of two polypeptide chains, termed the A chain and the B chain, linked together by disulfide bonds formed between cysteine residues. The N-terminal group of the A chain is a glycine residue (GlyA1), and the N-terminal group of the B chain is a phenylalanine residue (PheB1). Both N-terminal positions contain reactive free α-amino groups. Adjacent to the C-terminal group of the B chain is a lysine residue (LysB29), which has a free ε-amino group. It is believed that these free amino groups contribute to the problem of aggregation of insulin molecules, with their eventual precipitation, as will be discussed in more detail below.

The self-association of insulin into dimers, hexamers, high molecular weight aggregates, and insoluble fibrils (at therapeutic concentrations) has been recognized as a problem in the treatment of diabetes mellitus, J. Brange, Galenics of Insulin (1987), especially in formulations intended for implantable insulin pumps. It seems that this process requires the presence of monomeric insulin with a concomitant change of its conformation, J. Brange et al., Studies of the Insulin Fibrillation Process, in Advanced Models for the Therapy of Insulin-Dependent Diabetes 85–90 (P. Brunetti & W. Waldhausl eds. 1987); V. Sluzky et al., 88 Proc. Nat'l Acad. Sci. USA 9377–9381 (1991), and is promoted by contacts with hydrophobic surfaces, W. D. Loughseed et al., 32 Diabetes 424–432 (1983), often present in insulin pumps. Attempts to stabilize insulin solutions have included the use of additives such as phenol derivatives, U. Derewenta et al., 338 Nature 594–596 (1989), nonionic and ionic surfactants, propylene glycol, glycerol, carbohydrates, and even calcium ions, J. Brange, Galenics of Insulin (1987). Sugar-based nonionic detergents have proven to be very efficient stabilizers. L. Hovgaard et al., 19 J. Controlled Release 135–138 (1992); V. Sluzky et al., 40 Biotechnol. Bioeng. 895–903 (1992).

The chemical modification of insulin through glycosylation at the three available amino groups (GlyA1, PheB1, and LysB29) has been described. S. Y. Jeong et al., 1 J. Controlled Release 57–66 (1984); U.S. Pat. Nos. 4,444,683; 4,478,746; 4,478,830; 4,483,792; 4,489,063; 4,489,064; 4,536,572. This modified insulin was evaluated extensively as a component for a glucose-responsive artificial pancreas using concanavalin A. S. Y. Jeong et al., 2 J. Controlled Release 143–152 (1985). It was hypothesized that glycosylation of amino groups, especially at the PheB1 and LysB29 sites, should lead to insulin derivatives with a suppressed tendency to self-associate. This is due to the fact that LysB29 is located on the edge of the dimerization surface of the monomer, and PheB1 is involved in the assembly of three dimers into insulin hexamers. T. L. Blundell et al., 26 Adv. Protein Chem. 279–402 (1972). It has been shown that monomeric or dimeric insulin derivatives, S. E. Shoelson et al., 31 Biochemistry 1757–1767 (1992); J. Brange et al., 333 Nature 679–682 (1988), when administered parenterally exhibit faster absorption profiles from the injection site and the intravenous profile is more attuned to endogenous insulin release. J. Brange et al., 13 Diabetes Care 923–94 (1990). Moreover, by incorporating the covalently bound carbohydrate onto the insulin molecule, the nonspecific hydrophobic aggregation process may be reduced by hydrophilization of its surface, while maintaining the bioactivity of the insulin derivative.

The physical stabilization of insulin by covalent attachment of p-succinylamidophenyl glucopyranoside (SAPG) groups to insulin resulted in seven glycosylated insulin derivatives: three monosubstituted, three disubstituted, and one trisubstituted. M. Baudyš et al., Physical Stabilization of Insulin by Glycosylation, 84 J. Pharm. Sci. 28–33 (1995). Nearly all of these derivatives retained in vivo biological activity comparable to insulin, the sole exception being the GlyA1-LysB29-disubstituted derivative, which yielded about 65% of the activity of native insulin. Protein self-association was most suppressed and physical stability was most improved with the disubstituted derivatives, especially those substituted at PheB1, and the trisubstituted derivative.

In view of the foregoing, it will be appreciated that an improved method for synthesis of insulin derivatives and certain insulin derivatives prepared by this or other methods would be a significant advancement in the art.

BRIEF SUMMARY OF THE INVENTION

It is an object of the present invention to provide an improved method for the synthesis of insulin derivatives wherein the process can be carried out without the need to isolate and purify intermediates, i.e. a "one-pot" method.

It is also an object of the invention to provide insulin derivatives wherein only the α-amino group of the PheB1 residue is linked to a polyethylene glycol moiety or derivative thereof.

It is another object of the invention to provide insulin derivatives wherein only the α-amino group of the PheB1 residue is linked to a glycoside.

These and other objects can be achieved by providing a method for the synthesis of an insulin derivative having a hydrophilic compound coupled to the PheB1 amino group comprising:

(a) coupling an acyl protective group to the GlyA1 and LysB29 amino groups of insulin comprising reacting insulin with a cyclic anhydride of a dicarboxylic acid in the presence of a tertiary amine thereby obtaining Gly-$N^{\alpha A1}$, Lys$N^{\epsilon B29}$-disubstituted insulin;

(b) reacting the Gly-$N^{\alpha A1}$, Lys$N^{\epsilon B29}$-disubstituted insulin with an activated hydrophilic compound thereby covalently bonding the hydrophilic compound to the PheB1 amino group;

(c) quantitatively hydrolyzing the acyl protective group from the GlyA1 and LysB29 residues, thereby obtaining the insulin derivative having the hydrophilic compound coupled to the PheB1 amino group.

In a preferred embodiment of the invention the cyclic anhydride of a dicarboxylic acid is a member selected from the group consisting of maleic anhydride, citraconic anhydride, phthalic anhydride, exo-cis-3,6-endoxo-$\Delta^4$-tetrahydrophthalic anhydride, and mixtures thereof. In another preferred embodiment of the invention, the tertiary amine is a member selected from the group consisting of triethylamine and N-methylmorpholine. The activated hydrophilic compound is preferably a derivative of polyethylene glycol represented by the formula:

$$(R-(O-CH_2CH_2)_n)_m-X$$

wherein R is hydrogen or lower alkyl having from about 1 to 6 carbon atoms; n is an integer from about 3 to about 400; m is an integer of 1 or 2; and X is a connecting spacer with a reactive end group having the formula:

$$-O-(CH_2)_r-COCl$$

where r is an integer from 1 to about 6; or $$-O-(CH_2)_r-SO_2Cl$$

where r is an integer from 1 to 6; or $$-O-CH_2CH_2-O-SO_2CH_2CF_3$$

or

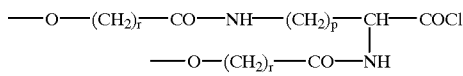

wherein r is an integer from 1 to about 6 and p is an integer from 1 to about 8; or

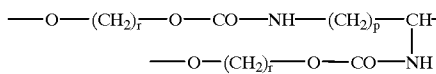

wherein r is an integer from 1 to about 6 and p is an integer from 1 to about 8.

The step of quantitatively hydrolyzing the acyl protective group from the GlyA1 and LysB29 residues preferably comprises mild acid treatment, more preferably treatment with dilute acetic acid, and most preferably treatment with a medium comprising 1 M acetic acid and 7 M urea.

Another preferred embodiment of the invention comprises an insulin derivative wherein a hydrophilic compound is coupled to the PheB1 amino group wherein the insulin derivative is prepared according to the method described above.

Still another preferred embodiment of the invention comprises an insulin derivative represented by the formula:

$$\text{Insulin-X-(PEG)}_m$$

wherein X is an organic spacer and PEG is a polyethylene glycol or alkoxy derivative thereof or a branched or dendrimeric derivative thereof, m is 1 or 2, and X is covalently coupled to the PheB1 residue of Insulin.

Preferably, the organic spacer is a member of the group consisting of $$-O-(CH_2)_r-CO-$$

wherein r is an integer from 1 to about 6;

$$-O-(CH_2)_r-SO_2-$$

wherein r is an integer from 1 to 6;

$$-O-CH_2CH_2-;$$

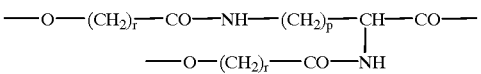

wherein r is an integer from 1 to 6 and p is an integer from 1 to 8; and

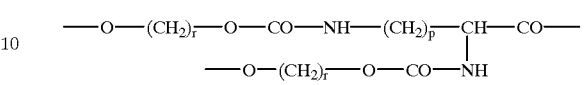

wherein r is an integer from 1 to 6 and p is an integer from 1 to 8. Further, the PEG moiety is preferably represented by the formula $R-(O-CH_2CH_2)_n-$ wherein R is hydrogen or lower alkyl, and n is an integer from 1 to about 400. In another preferred embodiment, the PEG moiety is a dendrimeric PEG based on a one- to six-fold consecutive bifurcation, more preferably on a three-fold consecutive bifurcation, such as a PEG represented by the formula:

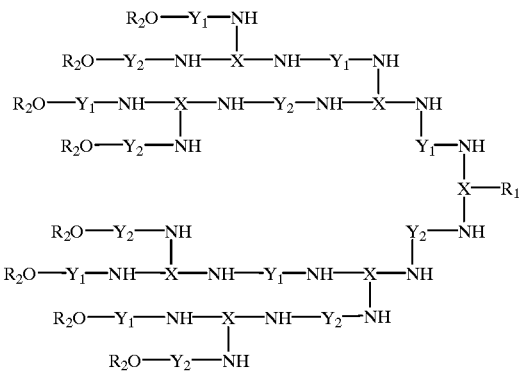

wherein $R_1$ is $-OH$ or $-NH-(CH_2)_m-COOH$; m is an integer from 1 to 10; $R_2$ is H or lower alkyl;

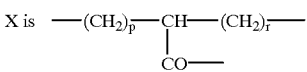

wherein the carbonyl group is linked to $R_1$ or $-NH-Y_1$ or $-NH-Y_2$; and p and r are integers from 0 to about 5; $Y_1$ and $Y_2$ are $-(CH_2)_k-(O-CH_2CH_2)_n-CO-$ or $-(CH_2)_k-(O-CH_2CH_2)_n-O-CO-$ wherein n is an integer from 0 to about 400 and is not generally equal for $Y_1$ and $Y_2$, and k is an integer from 1 to about 6 and is not generally equal for $Y_1$ and $Y_2$ and where the carbonyl group of $Y_1$ and $Y_2$ is linked to $-NH-$ which is linked to $-(CH_2)_p$ or $-(CH_2)_r$ of X, and the other end of $Y_1$ and $Y_2$ is linked to $-NH-$ group which is linked to carbonyl group of X.

DETAILED DESCRIPTION

Figure 1:
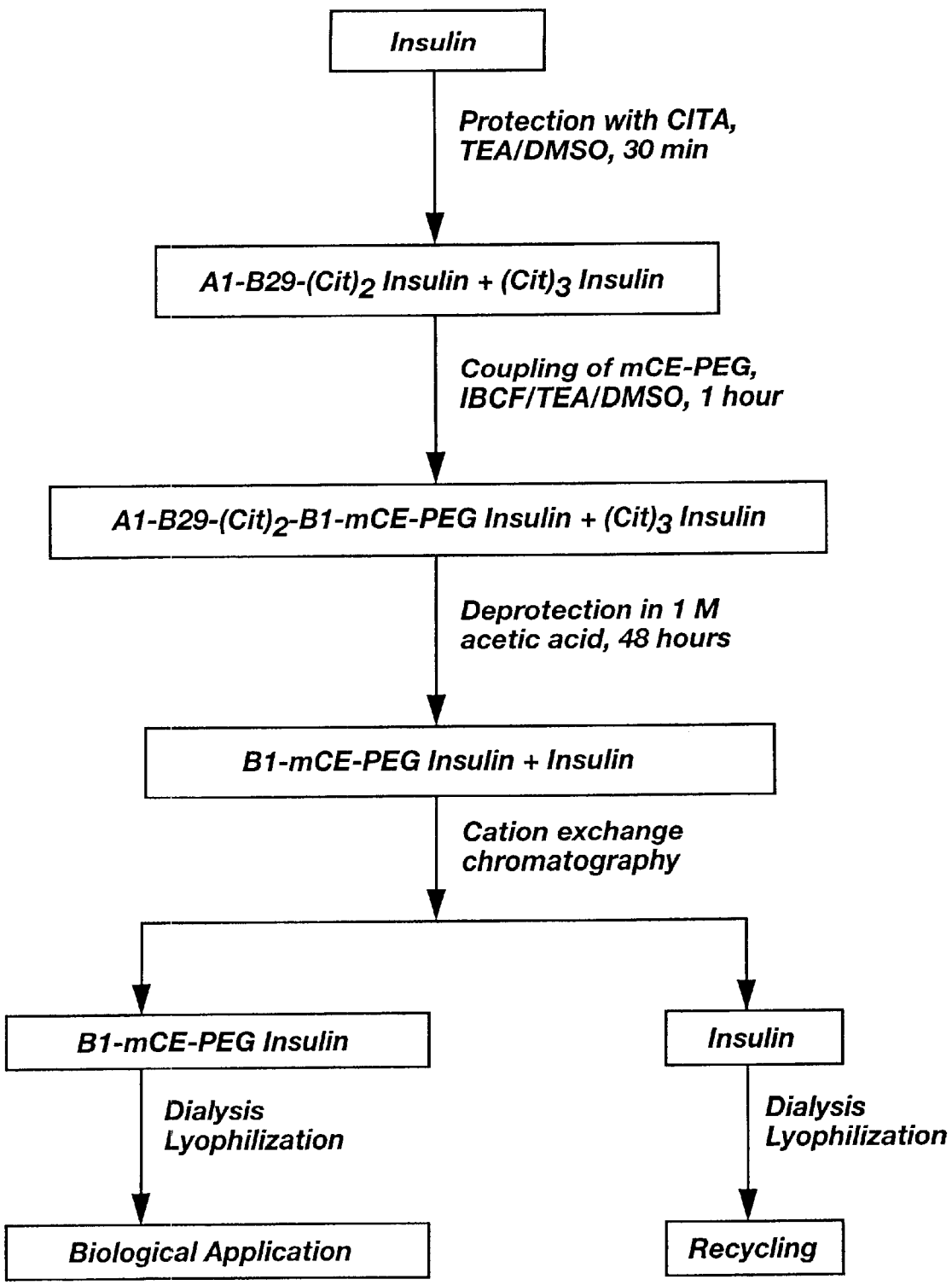
FIG. 1 shows a flow chart for the one-pot synthesis of PheB1-monomethoxymonocarboxyethylene polyethylene glycol (mCE-PEG) insulin and recycling of the major byproduct, citraconyl₃-insulin, and its conversion to insulin; CITA—citraconyl anhydride; TEA—triethylamine; IBCF—isobutylchloroformate; Cit—citraconyl.

Before the present method for the one-pot synthesis of insulin derivatives and compositions of matter wherein a polyethylene glycol moiety or derivative thereof or glycoside is linked to the PheB1 residue of insulin are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "an acyl protective group" includes a mixture of two or more of such acyl protective groups, reference to "a PEG" includes reference to one or more of such PEGs, and reference to "an organic spacer" includes reference to two or more of such organic spacers.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "HPLC" means high-performance liquid chromatography, i.e. wherein liquid chromatography is carried out under high pressure.

As used herein, "FPLC" means fast protein liquid chromatography, a type of HPLC wherein the instruments and surfaces are selected for compatibility with proteins.

As used herein, "pegylation" means derivatizing an entity by conjugation with polyethylene glycol or a derivative thereof.

As used herein, "PEG" means polyethylene glycol and derivatives thereof, such as, without limitation, branched and star polyethylene glycols such as are commercially available through Shearwater Polymers, Inc. (Huntsville, Ala.), alkoxy polyethylene glycols, and compounds represented by the formula:

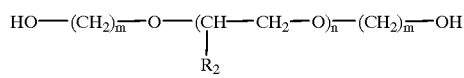

or

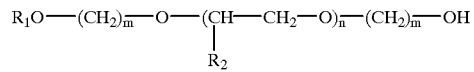

wherein $R_1$ is lower alkyl, $R_2$ is H or lower alkyl, m is an integer of about 2 to 12, and n is an integer of about 3 to 400, and the like. A more detailed description of illustrative PEGs that can be used according to the present invention is provided below.

As used herein, "lower alkyl" means a straight or branched saturated carbon chain of about 1 to 5 carbon atoms.

As used herein, "ELISA" means enzyme-linked immunosorbent assay.

One-Pot Method of Making Insulin Derivatives

A preferred embodiment of the invention comprises a method for the one-pot synthesis and purification of specific insulin derivatives having a hydrophilic moiety specifically coupled to the insulin PheB1 amino group (FIG. 1). As a starting material, insulins of diverse kinds, for example, pig, human, or bovine insulins can be used. Particular insulin derivatives that can be used are those containing protective groups in the $N^{\alpha A1}$ and $N^{\epsilon B29}$ positions. An illustrative $NH_2$-protecting group is an acyl group introduced by reacting cyclic anhydrides of dicarboxylic acids, such as maleic anhydride, citraconic anhydride, phthalic anhydride, exo-cis-3,6-endoxo-$\Delta^4$-tetrahydrophthalic anhydride, and their structural analogs, with insulin. It is known that these derivatives can be quantitatively prepared by dissolving insulin in appropriate solvents, such as dimethyl sulfoxide, dimethylformamide, pyridine, water, or mixtures thereof, and adding appropriate amounts of the protecting reagent (usually at a 1:2 molar ratio), preferably a cyclic anhydride of a dicarboxylic acid such as citraconic anhydride, in the presence of tertiary base such as triethylamine or N-methylmorpholine. The major product is Gly-$N^{\alpha A1}$, Lys-$N^{\epsilon B29}$ disubstituted insulin, which can be directly reacted with any activated hydrophilic compound specified above used in excess over insulin derivative (2 to 10 molar excess) without the need for isolation of the insulin intermediate. Since the protecting acyl groups specified above can be easily removed in aqueous, mildly acidic media, the resulting reaction mixture (1 volume) is intermixed with 1 M acetic acid containing 7 M urea (5 to 20 volumes) and left at room temperature until protecting acyl groups are quantitatively hydrolyzed. This complex mixture is applied directly to a cation exchange column such as an S-Sepharose HP column equilibrated with 1 M acetic acid containing 7 M urea, and the selected insulin derivative is then purified to homogeneity using a salt gradient (0 to 0.3 M NaCl). Further, insulin, which is the main byproduct, is simultaneously recovered.

The above-described synthetic scheme allows for "one pot" synthesis of PheB1 monosubstituted insulin without the need to isolate and purify intermediates. Thus, the overall yield of synthesized derivatives that can be achieved is up to 50% as compared to the starting amount of unmodified insulin. The yield of recovered insulin is around 30%, which can be recycled, further increasing the overall yield of synthesized PheB1 monosubstituted insulin derivatives. Moreover, the mildly acidic conditions used for removal of the dicarboxylic-acids-based protecting groups minimize side reactions that generally lower the final yield and complicate purification that again leads to low yields. In comparison, if the conventional t-Boc group is used for protection, it can be quantitatively removed only in trifluoroacetic acid, which dictates the necessity of isolating intermediates and also leads to side reactions, not to mention the need to use scavengers, all of which significantly lower the yield as compared to the presently described synthetic and purification scheme.

EXAMPLE 1

One-pot synthesis of PheB1-monomethoxymonocarboxyethyl-polyethylene Glycol (mCE-PEG Insulin Conjugate First, 100 mg of recombinant human insulin was dissolved in 2 ml of dry DMSO containing 100 µl of triethylamine, and then 4.2 mg of citraconic anhydride was added at room temperature. The mixture was stirred for 30 minutes (FIG. 1). Meanwhile, 85 µmol of monomethoxy-monocarboxyethylpolyethylene glycol (M. Wt. 600 or 2000) was dissolved in 2 ml of dry DMSO containing 8.6 mg of triethylamine, and then 11.7 mg of isobutylchloroformate was added at room temperature. After 5 minutes, the activated carboxyl PEG derivative was mixed with the insulin solution, and the mixture was stirred at room temperature for 2 additional hours. Protective citraconyl groups were removed by adding 6 ml of 7 M urea and 1.0 ml of glacial acetic acid (48 hours at room temperature). This mixture was directly applied to a HiLoad 26/10 SP Sepharose HP column equilibrated with 7 M urea, 1 M acetic acid, 0.01 M NaCl. The PheB1-mCE-PEG insulin conjugate was eluted with a gradient of NaCl (0.5% buffer B/min, wherein buffer B is 7 M urea, 1 M acetic acid, 0.3 M NaCl; flow rate 2.5–5.0 ml/min), collected, dialyzed against 0.01% NH$_4$HCO$_3$, and lyophilized.

Generally, the yield of PheB1-mCE-PEG-insulin prepared according to this procedure was about 50%, and the yield of the main byproduct, insulin (formed from tricitraconyl insulin), was about 30%. The insulin byproduct can be recycled.

PheB1 Monosubstituted Insulin Derivatives

Site-specific attachment of a hydrophilic moiety, preferably a polyethylene glycol derivative moiety or mono- or oligo-saccharide derivative moiety to the PheB1 amino group of insulin very substantially increases physical stability of such insulin derivatives in aqueous solutions and formulations for parenteral, as well as non-parenteral, administration. In contrast, attachment of hydrophilic groups to the GlyA1 and/or LysB29 amino groups of insulin has a much smaller impact on the increase of stability (only 2–3 fold) and is nonspecific. The mean fibrillation time (stabilization period) for PheB1 monosubstituted insulin derivatives in solution increases up to 50 times, while bioactivity of these derivatives is preserved. The immunogenicity and antigenicity of prepared insulin derivatives is either comparable to that of insulin for glycosyl insulin derivatives or is significantly reduced as found for polyethylene glycol-insulin derivatives. Also, pharmacodynamic and/or pharmacokinetic parameters can be improved, especially increased mean residence time for polyethylene glycol-insulin conjugates, ensuring necessary basal insulin levels in insulin-dependent diabetes mellitus (IDDM) patients. These insulin derivatives can be used as therapeutic drugs for treatment of diabetes.

A preferred embodiment of the invention comprises PheB1 substituted insulin derivatives wherein only the α-amino group of the insulin B-chain is linked to a polyethylene glycol derivative moiety or moieties, preferably monoalkylpolyethylene glycol or glycols, through a low molecular weight spacer, either linear (one PEG moiety) or branched or dendrimeric (2 or more PEG moieties). All these PEG-insulin conjugates have preserved bioactivity and significantly increased stability in aqueous solutions and formulations. Furthermore, these derivatives have improved pharmacokinetic behavior as reflected in increased mean residence time (increased half-life) and lower clearance rate. As generally accepted for any PEG-protein conjugate, these specific PEG-insulin conjugates have significantly attenuated immunogenicity and antigenicity.

The PEG derivatives used for insulin modification according to the present invention have the following general formula:

wherein R is hydrogen or lower alkyl having from about 1 to 6 carbon atoms, preferably 1; n is an integer from about 3 to about 400; m is an integer of 1 or 2; and X is a connecting spacer with reactive end groups having the formula:

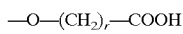

where r is an integer from 1 to about 6, preferably 2 to 3, and thus m is 1; or

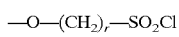

where r is an integer from 1 to 6, preferably 2, and thus m is 1; or

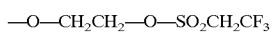

and thus m is 1; or

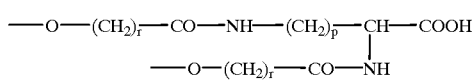

wherein r is an integer from 1 to 6, preferably 2 to 3, p is an integer from 1 to 8, and thus m is 2; or

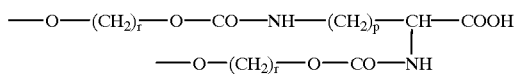

wherein r is an integer from 1 to 6, preferably 2 to 3, p is an integer from 1 to 8, and thus m is 2.

The carboxyl groups of the spacers set forth above can then be activated by one of the well known organic synthesis methods described in the open literature, preferably by the mixed anhydride or active ester method, to react specifically with the PheB1 insulin amino group of a particular insulin derivative to form an amide linkage. Alternatively, the reactive PEG-sulfonyl chloride described above can be reacted with the PheB1 amino group of a particular insulin derivative to form a sulfonamide linkage. Yet another activated PEG derivative, PEG-tresylate, described above, can be used and reacted specifically with the PheB1 amino group of a particular insulin derivative to form a direct C-N bond between the PEG chain and the PheB1 amino group, so there is no linker between the PEG moiety and the insulin molecule.

Also, the polyethylene glycol moiety attached to the PheB1 amino group by amide bond through the only —COOH group can be a highly branched, dendrimeric structure having the general formula:

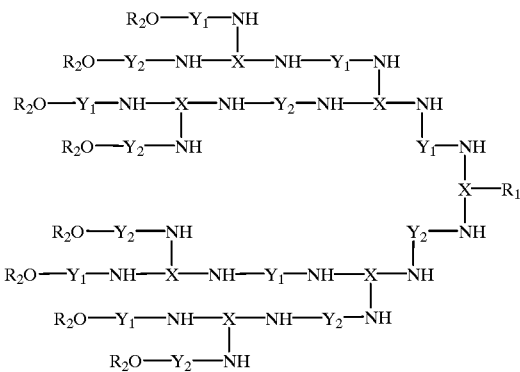

wherein $R_1$ is —OH or —NH—$(CH_2)_m$—COOH; m is an integer from 1 to 10; $R_2$ is H or lower alkyl having from 1 to about 6 carbon atoms;

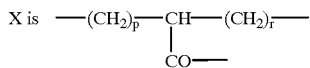

wherein the carbonyl group is linked to $R_1$ or —NH—Y, or —NH—$Y_2$; and p and r are integers from 0 to about 5; $Y_1$ and $Y_2$ are —$(CH_2)_k$—(O—$CH_2CH_2)_n$—CO— or —$(CH_2)_k$—(O—$CH_2CH_2)_n$—CO— wherein n is an integer from 0 to about 400 and is not generally equal for $Y_1$ and $Y_2$, and k is an integer from 1 to about 6 and is not generally equal for $Y_1$ and $Y_2$ and where the carbonyl group of $Y_1$ and $Y_2$ is linked to —NH— which is linked to —$(CH_2)_p$ or —$(CH_2)_r$ of X, and the other end of $Y_1$ and $Y_2$ is linked to —NH— group which is linked to carbonyl group of X.

The formula shown above for dendrimeric PEG is based on three-fold consecutive bifurcation. However, generally one- to six-fold consecutive bifurcation is also possible. Moreover, X can be more than trivalent, for example, tetra- or penta-valent having the following structures:

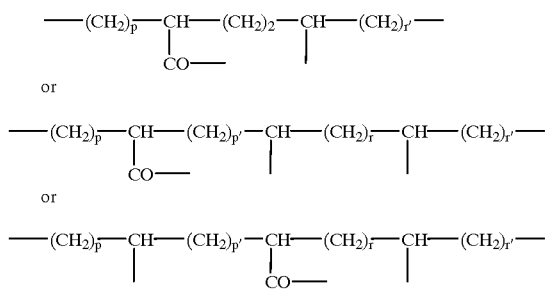

wherein p, p', r, and r' are integers from 0 to about 5, and unoccupied valences of these X groups are occupied by —NH—Y groups as specified above, and Y groups can be either identical or different from those specified above.

Another preferred embodiment of the invention comprises PheB1 monosubstituted insulin derivatives wherein only the α-amino group of the insulin B-chain is linked to a glycoside via a low molecular weight aglycon as generally but nonspecifically described for di- and tri-glycosylated insulin derivatives with a glycoside attached via GlyA1 and/or PheB1 and/or LysB29 amino groups by Kim, Jeong, and McRea in U.S. Pat. Nos. 4,444,683; 4,478,746; 4,478,830; 4,483,792; 4,489,063; 4,489,064; and 4,536,572. All such PheB1 monosubstituted insulin derivatives have preserved bioactivity and significantly increased physical stability in solution. Moreover, pharmacokinetic parameters for subcutaneous administration are identical to those of insulin, while pharmacodynamic parameters $C_{nadir}$ and $T_{nadir}$ are changed so that time-dependent blood glucose concentration response curve resembles intermediate acting insulin preparations. Immunogenicity and antigenicity of these derivatives are not changed and are comparable to those of insulin.

However, the carbohydrate moiety of the attached glycoside can be either any monosaccharide or oligosaccharide composed of about 2 to 8 monosaccharides in pyranose or furanose form. The type of glycoside can be O-glycoside, N-glycoside, or S-glycoside.

The aglycon that represents a spacer between the carbohydrate moiety and the insulin PheB1 amino group can be either one of those described in the above-cited patents or aliphatic spacers such as ε-aminocaproic acid or ε-aminocaprylic acid in N-glycosides of type N-(ε-aminocaproyl)-glycopyranosylamine or N-(ε-aminocapryloyl)-glycopyranosylamine. The only free amino group of these glycosides can be converted with thiophosgene into an isothiocyano group and reacted with the PheB1 amino group of a particular insulin derivative to form a thiocarbamoyl linkage. Alternatively, this amino group can be used for coupling a succinyl or glutaryl group, in the way of which, a carboxyl group is introduced by formation of N-(N'-ε-succinylamidocaproyl)-glycopyranosylamine or N-(N'-ε-succinylamidocapryloyl)glycopyranosylamine or N-(N'-ε-glutarylamidocaproyl)glycopyranosylamine or N-(N'-ε-glutarylamidocapryloyl)-glycopyranosylamine. This carboxylic group as well as carboxylic group of glycosides quoted in the above-mentioned patents can then be activated by one of the well known organic synthesis methods, particularly by a mixed anhydride method using isobutylchloroformate, to react specifically with the insulin PheB1 amino group of a particular insulin derivative to form an amide linkage.

Generally, any hydrophilic moiety, such as polyols, cyclic or linear, including hydrophilic polymers, such as polyvinylpyrrolidone or polyvinylalcohol having a molecular weight in the range of about 500–10,000 can be attached to the insulin PheB1 amino group through a low molecular weight linker (M. Wt. <300) to prepare biocompatible, stabilized insulin derivatives with improved pharmacokinetic and/or pharmacodynamic properties.

EXAMPLE 2

PEG-derivative-insulin conjugates, namely GlyA1-mCE-PEG insulin, GlyA1-PheB1-di-mCE-PEG insulin, GlyA1-LysB29-di-mCE-PEG insulin, and GlyA1-PheB1-LysB29-tri-mCE-PEG insulin, were prepared according to the method described below. One g (174 μmol) of human insulin was dissolved in 150 ml of water containing 1 mM $Na_2$EDTA by adjusting the pH to 7.5 with 0.1 M NaOH. An equal volume of DMF was added while stirring in an ice bath, and the pH was brought to 8.7. Meanwhile, 520 μmmol of mCE-PEG (M. Wt. 600 or 2000) was dissolved in 5 ml of dry DMF and 520 μmol of tributylamine and isobutylchloroformate was added. The mixture was stirred in an ice bath for 15 minutes, and then another 520 μmol of tributylamine was added. The resulting solution of activated carboxyl PEG derivative (mixed anhydride derivative) was slowly added to the insulin solution while stirring, and the pH was maintained between 8.5 and 8.8. After final pH adjustment, the mixture was left at room temperature for 1 hour. Finally, the solution was extensively dialyzed against 0.01% $NH_4HCO_3$ and lyophilized.

The freeze dried material was then fractionated by FPLC on a HiLoad 26/10 Q-Sepharose HP column. Usually, 200 mg of sample was dissolved in 20 ml of starting buffer (0.05 M Tris/HCl, 7 M urea, pH 7.95). To separate components, a linear gradient of buffer B (0.05 M Tris/HCl, 7 M urea, 0.2 M NaCl, pH 7.95) with a slope of 0.33% buffer B/min was applied. Flow rate was kept at 5 ml/min. Absorbance at 280 nm was continuously monitored, and the eluent from each peak was collected, acidified immediately to pH 6.0 with acetic acid, dialyzed first against water and then against 0.01% $NH_4HCO_3$, and, finally, lyophilized.

Final purification was achieved by fractionation on a Mono S HR 10/10 column. A sample (30 mg) was dissolved in 5 ml of buffer A (1 M acetic acid, 7 M urea, 0.01 M NaCl) and injected at a flow rate of 2.5 ml/min. To elute mCE-PEG insulin conjugates, a linear gradient of buffer B (1 M acetic acid, 7 M urea, 0.3 M NaCl) with a slope of 1% B/min was applied. Major peaks of PEG-insulin derivatives were collected, dialyzed first against water and then against 0.01% $NH_4HCO_3$, and finally dialyzed.

EXAMPLE 3
Physical Stability and Biologcal Activity of mCE-PEG Insulin Conjugates The long term physical stability of PEG-insulin derivatives was examined by their tendency to form fibrils in the accelerated shaking test at a concentration of 87 μM. Aggregation was evaluated in 5 ml borosilicate glass vials (1.2 ml filling volume) at 37° C., in a shaker at 100 strokes/min. Individual vials (n=14) were withdrawn at determined times, and the remaining soluble fraction of particular PEG-insulin derivatives was determined after filtration (PVDF membrane, 0.22 μm) using UV spectroscopy and/or HPLC. In parallel, vials were checked visually on a daily basis for the presence of turbidity and/or a precipitate, which was an independent indication that physical aggregation had occurred. Stability data for different mCE-PEG insulin conjugates are shown in Table 1. The most pronounced increase in stability was due to site-specific pegylation of the PheB1 amino group. The length of the PEG chain does not play a significant role in stabilization.

Figure 2:
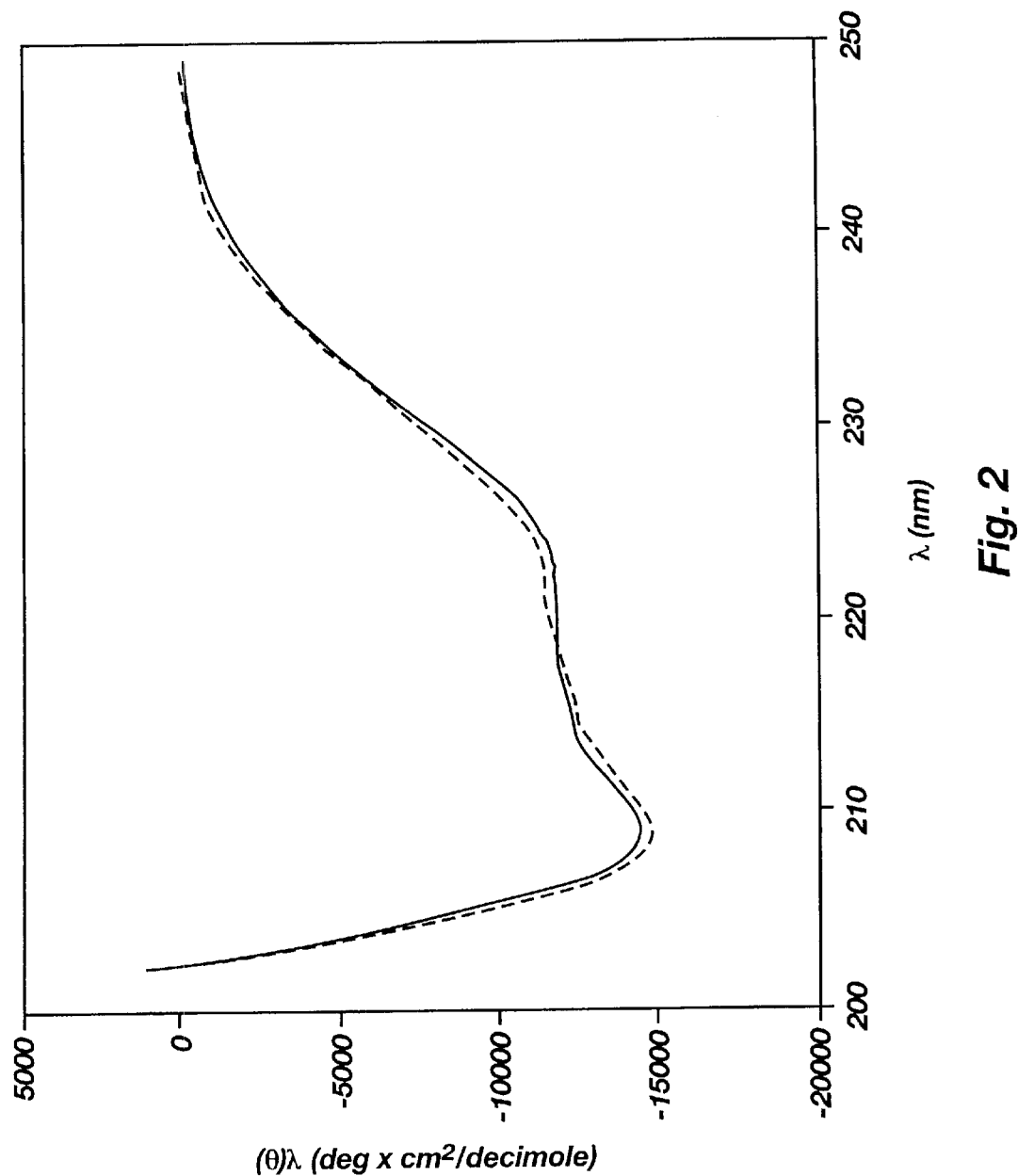
FIG. 2 shows far-UV circular dichroism (CD) spectra for Zn-free insulin (solid line) and PheB1-monomethoxymonocarboxyethylpolyethylene glycol insulin (broken line) in PBS, pH 7.4, at a concentration of 84 μM.

The biological activity of mCE-PEG-substituted insulin conjugates was tested in a rat model (male Sprague-Dawley rats, 250±50 g) by measuring blood glucose depression levels. The animals were fasted overnight (16 hours) prior to the experiment. In the morning, the rats were anesthetized with intraperitoneally administered sodium pentobarbital. Each animal received an i.v. injection (tail vein) of the particular insulin derivative (20 μg/ml NS/kg). Blood samples were taken from the jugular vein 15 and 5 minutes before injection and 15, 30, 60, 90, 120, 180, and 240 minutes after injection. Blood glucose levels were measured with an Accucheck III blood glucose monitor (Boehringer Mannheim). Bioactivities of insulin derivatives were calculated from AUC (area under curve) values, and the AUC value for the same dose of unmodified human insulin. In vivo experiments showed (Table 1) that bioactivity for monosubstituted PEG600 derivatives was preserved. Increasing the number of PEG600 moieties attached to insulin had a negative effect on bioactivity (Table 1). A similar decrease in bioactivity was observed if the molecular weight of PEG was increased to 2000. The far-UV CD spectra of mCE-PEG insulin conjugates did not detect any structural changes caused by the attachment of PEG groups, i.e. they were identical to a Zn-free insulin CD spectrum (FIG. 2).

TABLE 1

Physical Stability and Biological Activity of mCE-PEG-Insulin Conjugates

| mCE-PEG-Insulin Derivative | Days to Precipitation[a] ± S.D. | Biological Activity[b] (IU/mg ± S.D.) |
|---|---|---|
| Zn-free Insulin | 0.5 ± 0.2 | 25.2 ± 4.7 |
| A1-PEG600 Insulin | 4.7 ± 1.7 | 22.2 ± 4.2 |
| B1-PEG600 Insulin | 22.0 ± 4.6 | 22.8 ± 4.2 |
| A1-B1-(PEG600)2 Insulin | 26.4 ± 4.6 | 16.2 ± 3.2 |
| A1-B29-(PEG600)2 Insulin | 8.4 ± 1.3 | 19.1 ± 3.6 |
| A1-B1-B29-(PEG600)3 Insulin | 35.9 ± 5.3 | 5.3 ± 1.1 |
| A1-PEG2000 Insulin | 4.8 ± 1.2 | 15.7 ± 3.1 |
| B1-PEG2000 Insulin | 26.9 ± 4.9 | 15.4 ± 2.6 |
| A1-B1-(PEG2000)2 Insulin | 19.3 ± 2.3 | ND[c] |
| A1-B29-(PEG2000)2 Insulin | 6.6 ± 1.5 | 10.6 ± 2.1 |

[a]Determined for 87 μM concentration of each derivative.
[b]The biological activity of each derivative was determined with at least six animals. Solutions were freshly made in PBS (20 μg sample/ml) and biological activity determined.
[c]Not determined.

EXAMPLE 4
PheB1-p(succinylamido)-phenyl-α-D-glucopyranoside (SAPG) Insulin Conjugate (PheB1-SAPG insulin) and Other SAPG Insulin Conjugates First, 100 mg of di-$N^{\alpha A1}$, $N^{\epsilon B29}$-Boc insulin (human recombinant), prepared according to the procedure of 266 J. Biol. Chem. 18814–18818 (1991), was dissolved in 10 ml of dry dimethyl sulfoxide (DMSO) and 100 μl of tributylamine added. A 5–10 molar excess of the mixed anhydride derivative of SAPG to insulin in 1.6 ml of dimethylformamide (DMF) was added and the solution stirred at room temperature for 3 hours. The mixed anhydride derivative of SAPG was synthesized according to M. Baudyš et al., Physical Stability of Insulin by Glycosylation, 84 J. Pharm. Sci. 28–33 (1995). The resulting insulin conjugate was precipitated in excess dry acetone, dialyzed against 0.01% $NH_4HCO_3$ and lyophilized. The lyophilizate was dissolved in 10 ml trifluoroacetic acid with 5% anisole as a scavenger and kept under $N_2$ at 0° C. up to 1 hour to remove Boc groups. The resulting deprotected insulin derivative was precipitated with dry ether. Purification was carried out by cation exchange chromatography on HiLoad SP-Sepharose HP column essentially as described in M. Baudyš et al., Physical Stability of Insulin by Glycosylation, 84 J. Pharm. Sci. 28–33 (1995).

Other SAPG insulin conjugates, specifically, GlyA1-monoSAPG, LysB29-monoSAPG, GlyA1-Lys29-diSAPG, GlyA1-PheB1-diSAPG, PheB1-LysB29-diSAPG, and GlyA1-PheB1-LysB29-triSAPG insulin conjugates were also synthesized and purified in a similar manner, essentially as described in M. Baudyš et al., Physical Stability of Insulin by Glycosylation, 84 J. Pharm. Sci. 28–33 (1995).

EXAMPLE 5
Physical Stability of SAPG Insulin Conjugates and Their Concentration Dependency SAPG insulin derivatives were dissolved in PBS, pH 7.4, at concentrations of 85, 170, 340, and 680 μM. Zn-insulin, as well as Zn-free insulin solutions prepared in the same manner were used as controls. The aggregation was evaluated in 5 ml borosilicate glass vials (1.2 ml filling volume) at 37° C., in a shaker at 100 strokes/min. Individual vials (n=14) were withdrawn at determined times, and the remaining soluble fraction of particular SAPG insulin derivative was determined after filtration (PVDF membrane, 0.22 μm) using UV spectroscopy and/or HPLC. In parallel, vials were checked visually on a daily basis for the presence of turbidity and/or precipitation, which is an independent indication that physical aggregation has occurred. Stability data for different SAPG insulin derivatives are summarized in Table 2.

TABLE 2

Concentration Dependency of Physical Stability of SAPG-Insulin Derivatives

| SAPG-Insulin Derivative | Days to Precipitation (S.D.[a]) | | | |
|---|---|---|---|---|
| | 85 μM | 170 μM | 340 μM | 680 μM |
| Zn-insulin | 0.3 (0.1) | 0.3 (0.1) | 0.3 (0.1) | 0.3 (0.1) |
| Zn-free insulin | 0.6 (0.2) | 1.0 (0.5) | 1.0 (0.5) | 1.2 (0.3) |
| A1-SAPG insulin | 3.4 (2.3) | 2.2 (0.3) | 1.7 (0.4) | 1.2 (0.7) |
| B1-SAPG insulin | 12.7 (2.9) | 11 (3.7) | 9.8 (3.0) | 9.6 (3.5) |
| B29-SAPG insulin | 1.0 (0.5) | 0.6 (0.3) | — | — |
| A1-B1-diSAPG insulin | 19.6 (4.1) | 10.0 (4.2) | 6.8 (0.9) | 3.6 (1.8) |
| A1-B29-diSAPG insulin | 4.9 (4.3) | 3.5 (1.3) | — | — |
| B1-B29-diSAPG insulin | 15.9 (4.2) | 8.2 (1.0) | 6.6 (0.6) | 6.6 (0.6) |
| A1-B1-B29-triSAPG insulin | 17.3 (9.1) | 10.4 (7.0) | 3.4 (0.8) | 2.4 (0.8) |

[a]S.D.-Standard deviation

Figure 3:
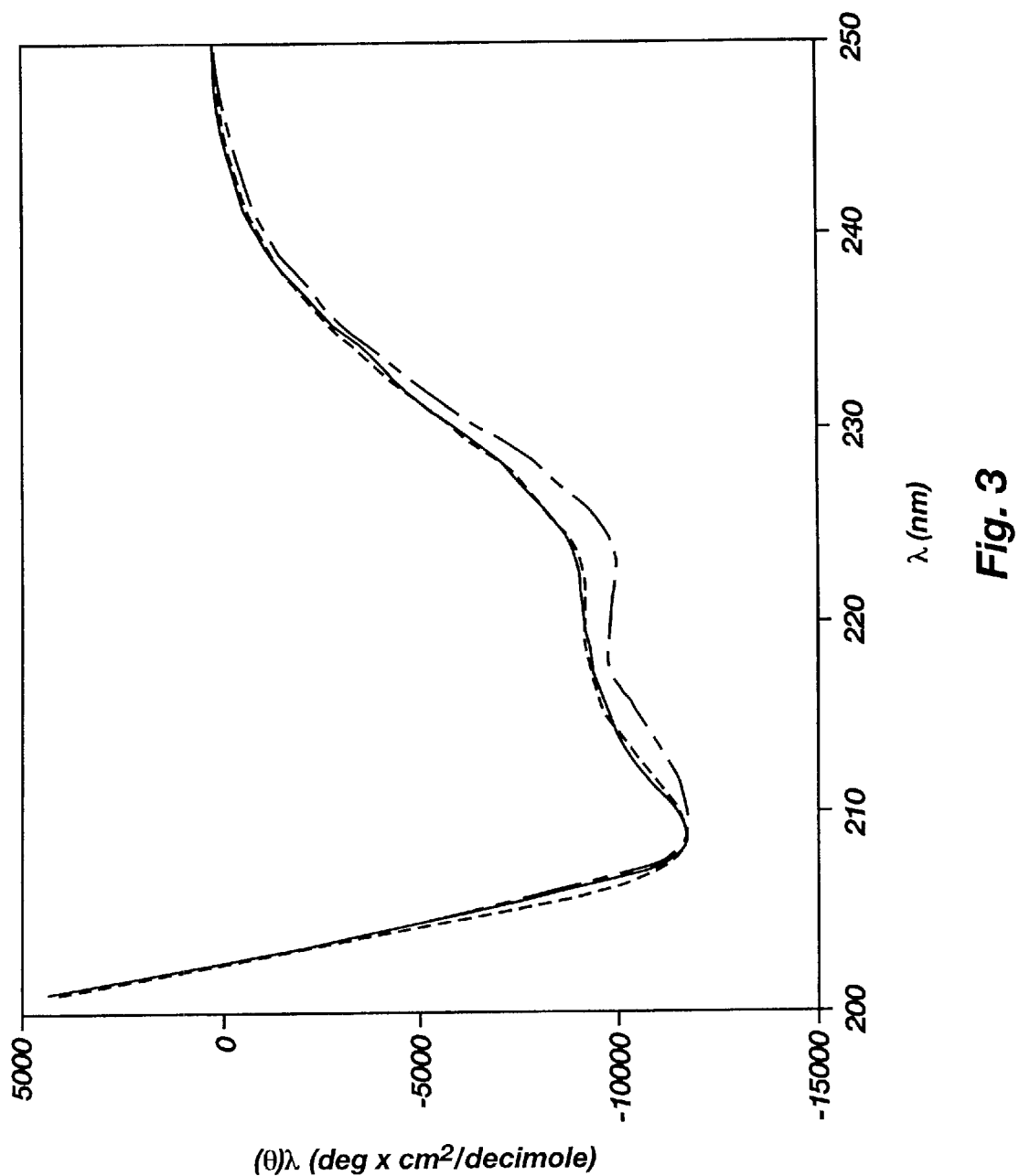
FIG. 3 shows far-UV CD spectra of Zn-insulin (-.-), Zn-free insulin (...) PheB1-SAPG-insulin nonstressed (—), and PheB1-SAPG-insulin stressed for 9 days in a shaking test in PBS, pH 7.4, at a concentration of 85 $\mu$M (---).

Evidently, the most pronounced increase in stability in pharmaceutically relevant concentration range (0.5 to 4.0 mg/ml) is due to selective glucosylation of the insulin PheB1 amino group. Glucosylation (SAPG moiety attachment) of additional insulin amino groups causes the decrease in stabilization period, especially at insulin derivative concentration higher than 1.0 mg/ml. In FIG. 3, the far-UV CD spectrum of freshly made PheB1-SAPG-insulin solution is compared to the identical sample stressed for 9 days (100 strokes/min) in which no macroscopic fibrillation and/or precipitation had yet occurred. Since the spectra are identical, no changes in secondary and/or tertiary structure occurred during hydrodynamic stress. Moreover, the CD spectrum of Zn-free insulin is also identical, which implies that no spatial or structural changes occurred due to the attachment of the SAPG moiety. Similar results were obtained for other SAPG insulin derivatives.

Independent verification of structural integrity for the post-stressed, nonfibrillated samples were obtained from in vivo assays. The biological activity of three different PheB1-SAPG substituted insulin conjugates was tested in a rat model (male Sprague-Dawley rats, 250±50 g) by measuring blood glucose depression levels. The animals were fasted overnight (16 hours) prior to the experiment. In the morning, the rats were anesthetized with intraperitoneally administered sodium pentobarbital. Each animal received an intravenous (IV) injection (tail vein) of the particular insulin derivative (20 μg/ml NS/kg). Blood samples were taken from the jugular vein 15 and 5 minutes before injection and 15, 30, 60, 90, 120, 180, and 240 minutes after injection. Blood glucose levels were measured with an Accucheck III blood glucose monitor (Boehringer Mannheim). Bioactivities of insulin derivatives were calculated from AUC (area under the curve) values, and the AUC value for the same dose of unmodified human insulin. The results are shown in Table 3. No significant differences in biological activity of pre- and post-stressed samples were found.

TABLE 3

Biological Activity of SAPG-Insulin Derivatives

| SAPG-Insulin Derivative | Biological Activity[a] ± S.D. Nonstressed Samples[b] | Biological Activity[a] ± S.D. Stressed Samples[c] |
|---|---|---|
| Zn-free insulin | 25.2 ± 4.7 | — |
| A1-SAPG-insulin | 22.2 ± 4.2 | — |
| B1-SAPG-insulin | 24.0 ± 4.0 | 26.6 ± 4.4 |
| B29-SAPG-insulin | 24.2 ± 4.6 | — |
| A1-B1-diSAPG-insulin | 22.4 ± 3.9 | — |
| A1-B29-diSAPG-insulin | 16.8 ± 3.4 | — |
| B1-B29-diSAPG-insulin | 30.2 ± 5.6 | 27.8 ± 4.9 |
| A1-B1-B29-triSAPG-insulin | 19.9 ± 3.6 | 20.2 ± 3.5 |

[a]The biological activity of each derivative was determined with at least six animals.
[b]Solutions were freshly made in PBS (20 μg sample/ml) and biological activity determined.
[c]Samples were dissolved at a concentration of 0.5 mg/ml in PBS, pH 7.4, and shaken for 9 days at 37° C., 100 strokes/min, then diluted (20 μg/ml) and biological activity determined.

EXAMPLE 6

Immunogenicity of SAPG Insulin Conjugates and mCE-PEG Insulin Conjugates For Two Inbred Strains of Mice Inbred A/J and C57BL/10ScSn mice, 12 weeks old, were used throughout the experiments. Mice (10 per experimental group) were immunized intraperitoneally with 5 μg samples on day 0. Samples were injected either in soluble form (dissolved in PBS, pH 7.4) or as a precipitate (alum precipitate). After 3 weeks, the mice were given a secondary injection, and after another 3 weeks, a third injection. Eight days after the last immunization, the mice were exsanguinated and the serum was separated and stored at −80° C. The specific antibody level in the serum was determined by an ELISA indirect method as described in 44 J. Clin. Lab. Immunol. 191–241 (1994). The results are summarized in Table 4. While PheB1-SAPG-insulin conjugates showed mice in vivo immunogenic properties comparable to those of insulin, PheB1-mCE-PEG insulin conjugates had generally significantly attenuated or negligible immunogenicity as compared to insulin.

TABLE 4

Antibody Titres[a] Induced in Mice by SAPG- and mCE-PEG-Insulin Conjugates Applied Intraperitoneally

| Insulin Derivative | Formulation | Strain | |
|---|---|---|---|
| | | A/J | B10 |
| Zn-insulin | Soluble | 10.5 | 11.4 |
| | Alum ppt. | 12.7 | 12.7 |
| B1-SAPG-Insulin | Soluble | 10.8 | 9.1 |
| | Alum ppt. | 11.9 | 12.7 |
| B1-B29-diSAPG-Insulin | Soluble | 11.5 | 10.0 |
| | Alum ppt. | 11.8 | 10.1 |
| A1-B1-B29-triSAPG-Insulin | Soluble | 9.9 | 9.1 |
| | Alum ppt. | 12.4 | 11.2 |
| B1-PEG600-Insulin | Soluble | 0 | 0 |
| | Alum ppt. | 6.1 | 9.5 |
| B1-PEG2000-Insulin | Soluble | 0 | 0 |
| | Alum ppt. | 0 | 0 |
| A1-B1-B29-(PEG600)$_3$-Insulin | Soluble | 0 | 0 |
| | Alum ppt. | 0 | 0 |

[a]Expressed as $\log_2$ of serum dilution.

EXAMPLE 7
Pharmacokinetics and Pharmacodynamics of GlyA1-SAPG Insulin and PheB1-SAPG-insulin For pharmacokinetic (PK) and pharmacodynamic (PD) studies, mongrel male dogs weighing 25–30 kg were used. The dogs were fasted overnight, and anesthesia was induced by intravenous injection of 22 mg sodium pentobarbital/kg and further maintained by Halothan inhalation. A catheter was introduced into saphenous vein of the front leg and maintained with slow infusion (0.2 ml/min) of Ringer's solution. After the dog was stabilized, basal blood samples (3 ml) were taken at 15 and 5 minutes prior to the insulin administration. A Zn-insulin solution or SAPG-insulin solution (either GlyA1-SAPG-insulin or PheB1-SAPG-insulin) at 0.7 nmol/kg was administered subcutaneously (SC) or intravenously (IV). Blood samples were taken from the catheter at 10, 20, 30, 40, 50, 60, 75, 90, 105, 120, 150, 180, 210, 240, 300, and 360 minutes for SC injection, and at 1, 3, 5, 7, 10, 15, 20, 30, 40, 50, 60, 75, 90, 105, and 120 minutes for IV injection.

Blood glucose levels (BGL) were measured with an Accucheck III blood glucose monitor (Boehringer Mannheim). Plasma immunoreactive insulin levels were determined using Coat-A-Count insulin radioimmunoassay kit (Diagnostic Products Corporation, Los Angeles, Calif.). The GlyA1-SAPG-insulin and PheB1-SAPG-insulin standard curves were used to determine plasma levels for these insulin derivatives.

For the PD analysis, the area under the BGL depression versus time curve was calculated by the linear trapezoidal method, and the nadir BGL (% of basal level, $C_{nadir}$) and the time to $C_{nadir}$ ($t_{nadir}$) were determined from experimental data. For the PK analysis, the data were processed using statistical moment derived noncompartmental analysis to determine the mean residence time (MRT), mean absorption time (MAT, and bioavailability (F). The results are expressed as mean±SEM, and statistical comparisons have been made using Student's t-test for paired samples.

Figure 4A:
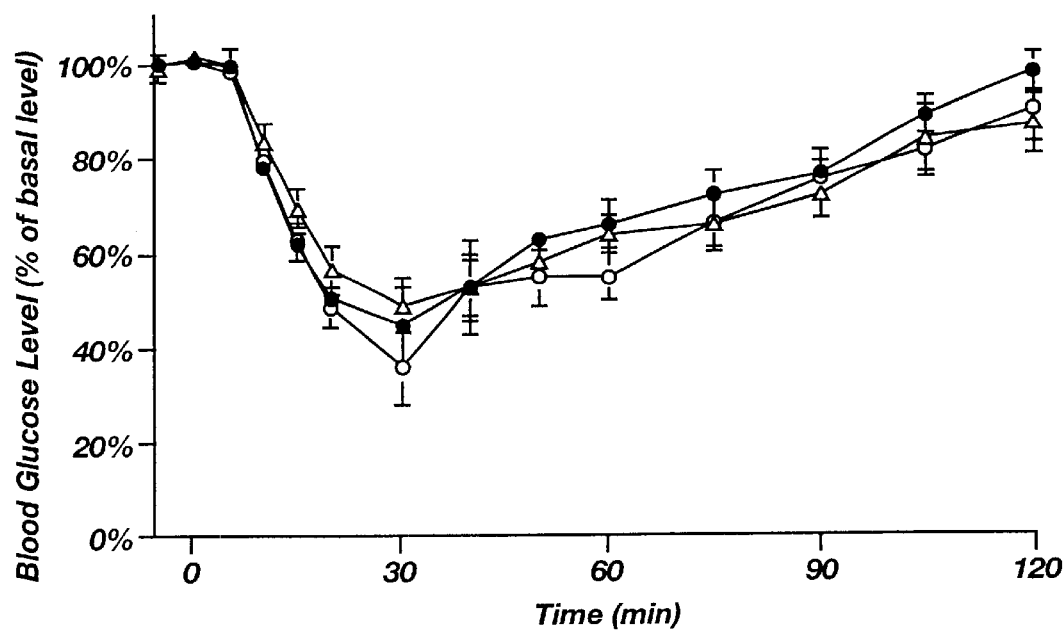
FIG. 4A shows blood glucose levels after intravenous (IV) administration of 0.7 nmol/kg of Zn-insulin (○), GlyA1-SAPG-insulin (Δ), or PheB1-SAPG-insulin (●) in 6 dogs (mean±SEM).
Figure 4B:
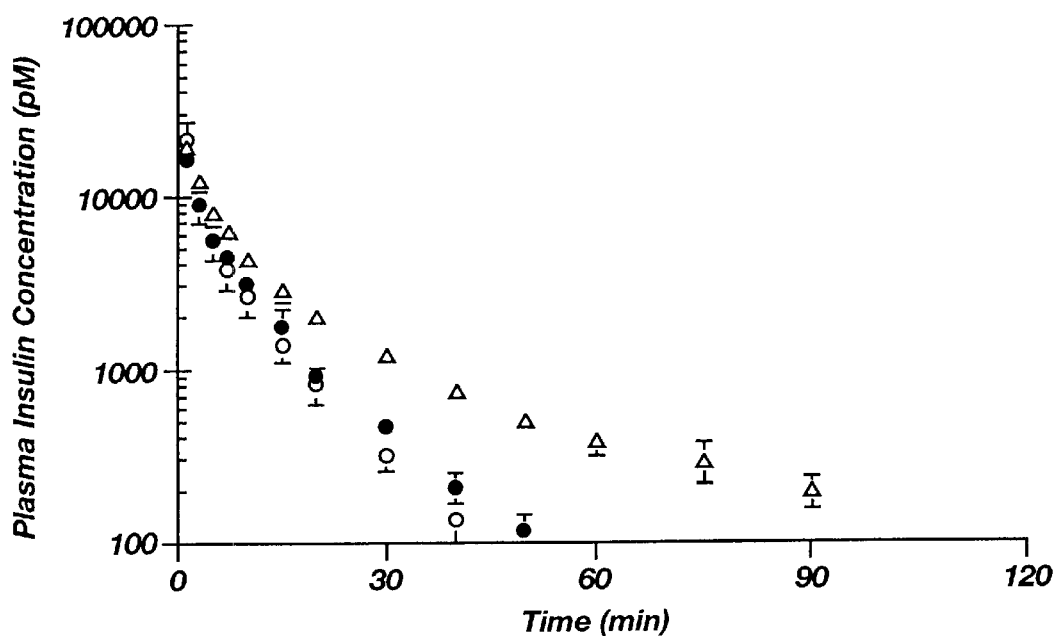
FIG. 4B shows a plasma insulin concentration after IV administration of 0.7 nmol/kg of Zn-insulin (○), GlyA1-SAPG-insulin (Δ), or PheB1-SAPG-insulin (●) in 6 dogs (mean±SEM).

FIG. 4A demonstrates that PD profiles of GlyA1-SAPG-insulin and PheB1-SAPG-insulin for the IV route of administration are not different from that of the insulin control. Consequently, there are no differences in IV pharmacodynamic parameters. PK profiles for Zn-insulin, GlyA1-SAPG insulin, and PheB1-SAPG-insulin are shown in FIG. 4B. While PheB1-SAPG-insulin PK parameters are not statistically different from those of Zn-insulin, GlyA1-SAPG-insulin PK parameters are significantly changed, especially clearance is slower (Table 5).

TABLE 5

Pharmacokinetic Parameters for A1-SAPG-Insulin and B1-SAPG-Insulin after Intravenous Administration in Dog

| Parameter | Zn-Insulin | A1-SAPG-Insulin | B1-SAPG-Insulin |
|---|---|---|---|
| AUC (nM × min) | 101 ± 23 | 177 ± 11[b] | 100 ± 6 |
| MRT (min) | 8.7 ± 0.9 | 19.8 ± 1.4[b] | 9.5 ± 0.6 |
| $CL_{total}$ (ml/min/kg) | 8.8 ± 2.0 | 4.0 ± 0.3[a] | 7.1 ± 0.5 |
| $V_{SS}$ (ml/kg) | 81 ± 22 | 80 ± 7 | 67 ± 5 |

AUC = area under the curve; MRT = mean residence time; CL = clearance; $V_{SS}$ = Volume of distribution; a – p < 0.05; b – p < 0.01.

Figure 5A:
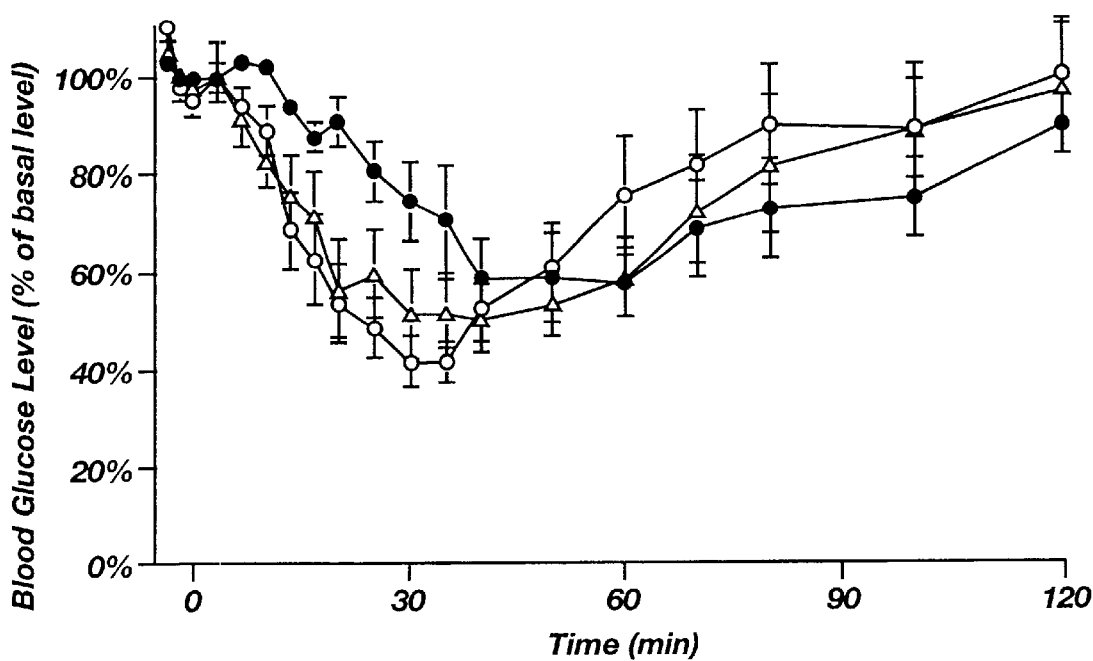
FIG. 5A shows blood glucose concentration change after subcutaneous (SC) administration of 0.7 nmol/kg of Zn-insulin (○), GlyA1-SAPG-insulin (Δ), or PheB1-SAPG-insulin (●) in 6 dogs (mean±SEM).

The mean BGL changes after SC administration of Zn-insulin, GlyA1-SAPG-insulin, and PheB1-SAPG-insulin are shown in FIG. 5A. After PheB1-SAPG-insulin injection, the BGL depression was delayed and prolonged compared to Zn-insulin administration. The PD parameters are summarized in Table 6.

TABLE 6

Pharmacodynamic Parameters for A1-SAPG-Insulin and B1-SAPG-Insulin after Subcutaneous Administration in Dog

| Parameter | Zn-Insulin | A1-SAPG-Insulin | B1-SAPG-Insulin |
|---|---|---|---|
| $AUC_G$ (mg/dl × min) | 8330 ± 1357 | 8091 ± 1483 | 6674 ± 1222 |
| $C_{nadir}$ (% of basal) | 35 ± 3 | 41 ± 5 | 51 ± 8[a] |
| $t_{nadir}$ (min) | 100 ± 19 | 130 ± 16 | 166 ± 16[a] |

$C_{nadir}$ = Decrease of concentration at nadir; $t_{nadir}$ = Time to nadir; a – p < 0.05.

Figure 5B:
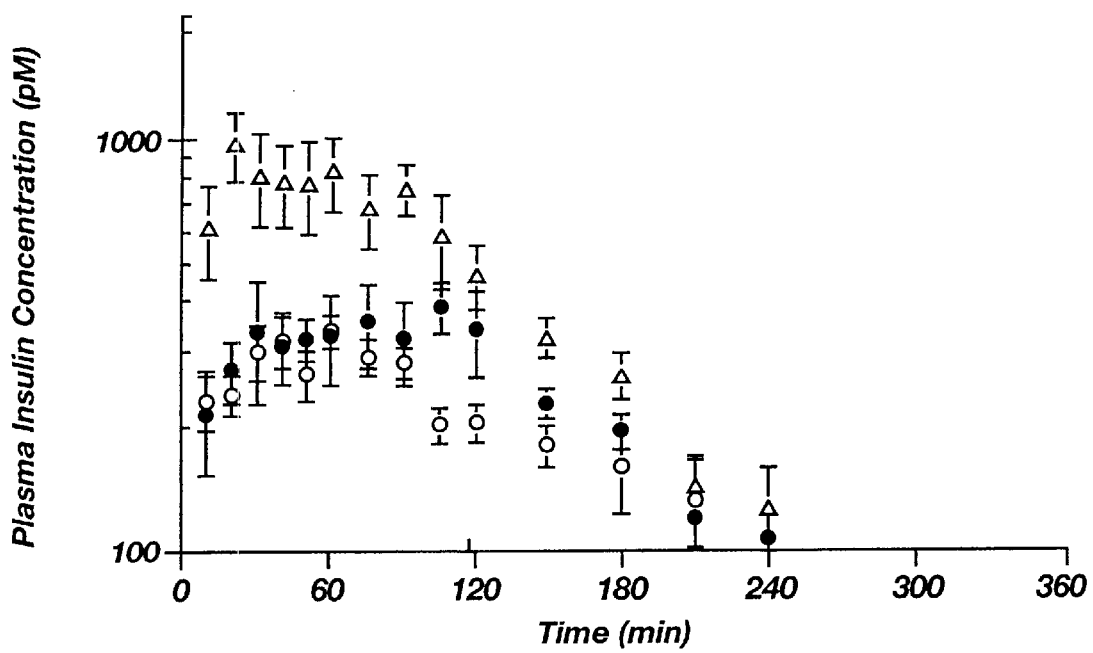
FIG. 5B shows plasma insulin concentration profiles after SC administration of 0.7 nmol/kg of Zn-insulin (○), GlyA1-SAPG-insulin (Δ), or PheB1-SAPG-insulin (●) in 6 dogs (mean±SEM).

There were no significant differences amongst samples in $AUC_G$ (area under the curve for BGL curve), but the $C_{nadir}$ and $t_{nadir}$ of PheB1-SAPG-insulin were significantly different from that of Zn-insulin. FIG. 5B shows plasma insulin levels after SC administration. As for the IV administration route, PheB1-SAPG-insulin exhibited a PK profile comparable to insulin while GlyA1-SAPG-insulin plasma concentration was markedly higher, reflecting its slower clearance as observed for IV administration route (Table 7). Thus, PheB1-SAPG-insulin has biological potency equal to Zn-insulin, and its PK parameters are not significantly different from those of Zn-insulin, while the PD profile shows a delayed response resembling short to intermediate acting insulin formulations/preparations.

TABLE 7

Pharmacokinetic Parameters for A1-SAPG-Insulin and B1-SAPG-Insulin after Subcutaneous Administration in Dog

| Parameter | Zn-Insulin | A1-SAPG-Insulin | B1-SAPG-Insulin |
|---|---|---|---|
| AUC (nM × Min) | 48 ± 3 | 113 ± 16[a] | 62 ± 9 |
| MRT (min) | 115 ± 8 | 100 ± 11 | 136 ± 7 |
| MAT (min) | 106 ± 8 | 80 ± 12 | 127 ± 7 |
| $CL_{total}$ (ml/min/kg) | 15.1 ± 1.4 | 6.5 ± 1.1[a] | 12.2 ± 1.5 |
| F | 0.60 ± 0.14 | 0.69 ± 0.15 | 0.62 ± 0.08 |

MAT = mean absorption time; F = bioavailability; a – p < 0.01.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

We claim:

1. A method for the synthesis of an insulin derivative having a hydrophilic compound coupled to the PheB1 amino group comprising:
    (a) coupling an acyl protective group to the GlyA1 and LysB29 amino groups of insulin comprising reacting insulin with a cyclic anhydride of a dicarboxylic acid in the presence of a tertiary amine thereby obtaining Gly-$N^{\alpha A1}$, LysN$^{\epsilon B29}$-disubstituted insulin;
    (b) reacting the Gly-$N^{\alpha A1}$, LysN$^{\epsilon B29}$-disubstituted insulin with an activated hydrophilic compound thereby covalently bonding the hydrophilic compound to the PheB1 amino group;
    (c) quantitatively hydrolyzing the acyl protective group from the GlyA1 and LysB29 residues, thereby obtaining the insulin derivative having the hydrophilic compound coupled to the PheB1 amino group.

2. The method of claim 1 wherein said cyclic anhydride of a dicarboxylic acid is a member selected from the group consisting of maleic anhydride, citraconic anhydride, phthalic anhydride, exo-cis-3,6-endoxo-$\Delta^4$-tetrahydrophthalic anhydride, and mixtures thereof.

3. The method of claim 2 wherein said cyclic anhydride of a dicarboxylic acid is maleic anhydride.

4. The method of claim 2 wherein said cyclic anhydride of a dicarboxylic acid is citraconic anhydride.

5. The method of claim 2 wherein said cyclic anhydride of a dicarboxylic acid is phthalic anhydride.

6. The method of claim 2 wherein said cyclic anhydride of a dicarboxylic acid is exo-cis-3,6-endoxo-$\Delta^4$-tetrahydrohthalic anhydride.

7. The method of claim 1 wherein said tertiary amine is a member selected from the group consisting of triethylamine and N-methylmorpholine.

8. The method of claim 7 wherein said tertiary amine is triethylamine.

9. The method of claim 1 wherein said activated hydrophilic compound is a derivative of polyethylene glycol represented by the formula:

wherein R is hydrogen or lower alkyl having from about 1 to 6 carbon atoms; n is an integer from about 3 to about 400; m is an integer of 1 or 2; and X is a connecting spacer with a reactive end group having the formula:

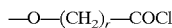

where r is an integer from 1 to about 6; or

where r is an integer from 1 to 6; or

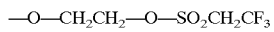

or

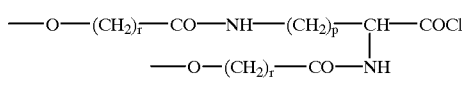

wherein r is an integer from 1 to about 6 and p is an integer from 1 to about 8; or

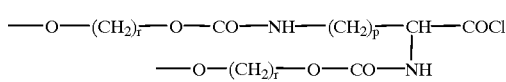

wherein r is an integer from 1 to about 6 and p is an integer from 1 to about 8.

10. The method of claim 1 wherein said quantitatively hydrolyzing the acyl protective group from the GlyA1 and LysB29 residues comprises mild acid treatment.

11. The method of claim 10 wherein said mild acid treatment comprises treatment with dilute acetic acid.

12. The method of claim 11 wherein said treatment with dilute acetic acid comprises treatment with a medium comprising 1 M acetic acid and 7 M urea.

13. An insulin derivative represented by the formula:

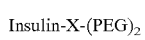

wherein X is

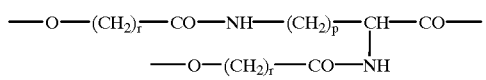

wherein r is an integer from 1 to 6 and p is an integer from 1 to 8, PEG is a polyethylene glycol or alkoxy derivative thereof or a branched or dendrimeric derivative thereof, and X is covalently coupled to the PheB1 residue of insulin.

14. The insulin derivative of claim 13 wherein PEG is represented by the formula:

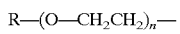

wherein R is hydrogen or lower alkyl, and n is an integer from 1 to about 400.

15. The insulin derivative of claim 13 wherein PEG is a branched derivative of polyethylene glycol or alkoxy derivative thereof.

16. An insulin derivative represented by the formula:

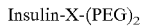

wherein X is an organic spacer, PEG is a dendrimeric derivative of polyethylene glycol or alkoxy derivative thereof based on a one- to six-fold consecutive bifurcation, and X is covalently coupled to the PheB1 residue of insulin.

17. The insulin derivative of claim 16 wherein PEG is a dendrimeric PEG based on a three-fold consecutive bifurcation.

18. The insulin derivative of claim 17 wherein PEG is represented by the formula:

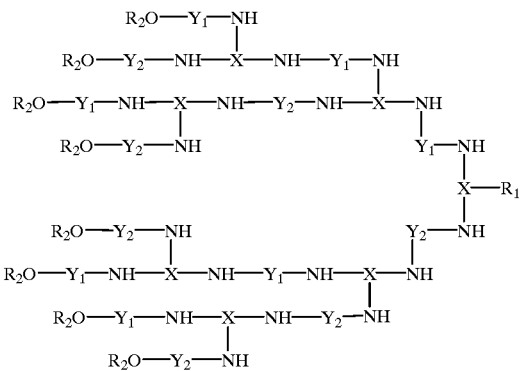

wherein $R_1$ is —OH or —NH—$(CH_2)_m$—COOH; m is an integer from 1 to 10;

$R_2$ is H or lower alkyl; X is 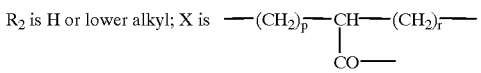

wherein the carbonyl group is linked to $R_1$ or —NH—$Y_1$ or —NH—$Y_2$; and p and r are integers from 0 to about 5; $Y_1$ and $Y_2$ are —$(CH_2)_k$—$(O-CH_2CH_2)_n$—CO— or —$(CH_2)_k$—$(O-CH_2CH_2)_n$—O—CO— wherein n is an integer from 0 to about 400 and can be the same or different in $Y_1$ and $Y_2$, and k is an integer from 1 to about 6 and can be the same or different in $Y_1$ and $Y_2$ and where the carbonyl group of $Y_1$ and $Y_2$ is linked to —NH— which is linked to —$(CH_2)_p$ or —$(CH_2)_r$ of X, and the other end of $Y_1$ and $Y_2$ is linked to —NH— group which is linked to carbonyl group of X.

19. The insulin derivative of claim 16 wherein said organic spacer is a member selected from the group consisting of

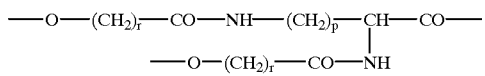

wherein r is an integer from 1 to 6 and p is an integer from 1 to 8; and

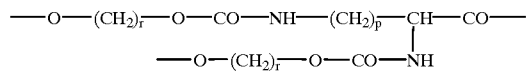

wherein r is an integer from 1 to 6 and p is an integer from 1 to 8.

20. The insulin derivative of claim 16 wherein PEG is represented by the formula:

$$R-(O-CH_2CH_2)_n-$$

wherein R is hydrogen or lower alkyl, and n is an integer from 1 to about 400.

* * * * *